United States Patent
Quake et al.

(10) Patent No.: US 7,670,471 B2
(45) Date of Patent: Mar. 2, 2010

(54) METHOD AND APPARATUS FOR ANALYSIS AND SORTING OF POLYNUCLEOTIDES BASED ON SIZE

(75) Inventors: Stephen R. Quake, Stanford, CA (US); Wayne D. Volksmuth, Menlo Park, CA (US)

(73) Assignee: California Institute of Technology, Pasadena, CA (US)

( * ) Notice: Subject to any disclaimer, the term of this patent is extended or adjusted under 35 U.S.C. 154(b) by 1160 days.

(21) Appl. No.: 11/255,795

(22) Filed: Oct. 21, 2005

(65) Prior Publication Data

US 2006/0035273 A1    Feb. 16, 2006

Related U.S. Application Data

(63) Continuation of application No. 10/021,850, filed on Dec. 13, 2001, now Pat. No. 6,964,736, which is a continuation of application No. 09/499,943, filed on Feb. 8, 2000, now Pat. No. 6,344,325, which is a continuation of application No. 08/932,774, filed on Sep. 23, 1997, now Pat. No. 6,221,654.

(60) Provisional application No. 60/026,693, filed on Sep. 25, 1996.

(51) Int. Cl.
*G01N 27/447* (2006.01)

(52) U.S. Cl. ..................... 204/452; 204/451

(58) Field of Classification Search ......... 204/450–455, 204/600–605
See application file for complete search history.

(56) References Cited

U.S. PATENT DOCUMENTS

| | | | |
|---|---|---|---|
| 2,656,508 A | 10/1953 | Coulter | |
| 4,581,624 A | 4/1986 | O'Connor | |
| 4,585,209 A | 4/1986 | Aine et al. | |
| 4,675,300 A | 6/1987 | Zare et al. | |
| 4,908,112 A | 3/1990 | Pace | |
| 4,963,498 A | 10/1990 | Hillman et al. | |
| 5,096,554 A | 3/1992 | Chin | |
| 5,126,022 A * | 6/1992 | Soane et al. | 204/458 |
| 5,140,161 A | 8/1992 | Hillman et al. | |
| 5,164,598 A | 11/1992 | Hillman et al. | |
| 5,271,724 A | 12/1993 | Van Lintel | |
| 5,304,487 A | 4/1994 | Wilding et al. | |
| 5,417,235 A | 5/1995 | Wise et al. | |
| 5,434,049 A | 7/1995 | Okano et al. | |
| 5,452,878 A | 9/1995 | Gravesen et al. | |
| 5,454,472 A | 10/1995 | Benecke et al. | |

(Continued)

FOREIGN PATENT DOCUMENTS

GB    2264496    9/1993

(Continued)

OTHER PUBLICATIONS

A. Moldavan, Science 80, 188 (1934).

(Continued)

*Primary Examiner*—Alex Noguerola
(74) *Attorney, Agent, or Firm*—Townsend and Townsend and Crew LLP

(57) ABSTRACT

The invention relates to a microfabricated device and methods of using the device for analyzing and sorting polynucleotide molecules by size.

13 Claims, 6 Drawing Sheets

U.S. PATENT DOCUMENTS

| | | | |
|---|---|---|---|
| 5,486,335 | A | 1/1996 | Wilding et al. |
| 5,498,392 | A | 3/1996 | Wilding et al. |
| 5,500,071 | A | 3/1996 | Kaltenbach et al. |
| 5,512,131 | A | 4/1996 | Kumar et al. |
| 5,558,998 | A | 9/1996 | Hammond et al. |
| 5,571,410 | A | 11/1996 | Swedberg et al. |
| 5,580,523 | A | 12/1996 | Bard |
| 5,589,136 | A | 12/1996 | Northrup et al. |
| 5,599,432 | A * | 2/1997 | Manz et al. ............... 204/451 |
| 5,632,876 | A | 5/1997 | Zanzucchi et al. |
| 5,637,469 | A | 6/1997 | Wilding et al. |
| 5,639,423 | A | 6/1997 | Northrup et al. |
| 5,641,400 | A | 6/1997 | Kaltenbach et al. |
| 5,646,039 | A | 7/1997 | Northrup et al. |
| 5,661,222 | A | 8/1997 | Hare |
| 5,681,484 | A | 10/1997 | Zanzucchi et al. |
| 5,702,618 | A | 12/1997 | Saaski et al. |
| 5,716,852 | A | 2/1998 | Yager et al. |
| 5,726,404 | A | 3/1998 | Brody |
| 5,726,751 | A | 3/1998 | Altendorf et al. |
| 5,750,015 | A | 5/1998 | Soane et al. |
| 5,757,482 | A | 5/1998 | Fuchs et al. |
| 5,800,690 | A | 9/1998 | Chow et al. |
| 5,833,926 | A | 11/1998 | Wurzel et al. |
| 5,852,495 | A | 12/1998 | Parce |
| 5,856,174 | A | 1/1999 | Lipshutz et al. |
| 5,863,801 | A | 1/1999 | Southgate et al. |
| 5,866,345 | A | 2/1999 | Wilding et al. |
| 5,869,004 | A | 2/1999 | Parce et al. |
| 5,880,071 | A | 3/1999 | Parce et al. |
| 5,885,470 | A | 3/1999 | Parce et al. |
| 5,904,824 | A | 5/1999 | Oh |
| 5,922,591 | A | 7/1999 | Anderson et al. |
| 5,932,100 | A | 8/1999 | Yager et al. |
| 6,221,654 | B1 | 4/2001 | Quake et al. |
| 6,344,325 | B1 | 2/2002 | Quake et al. |
| 6,818,395 | B1 | 11/2004 | Quake et al. |
| 6,833,242 | B2 * | 12/2004 | Quake et al. ............... 435/6 |
| 6,911,345 | B2 | 6/2005 | Quake et al. |
| 6,917,726 | B2 | 7/2005 | Levene et al. |
| 6,964,736 | B2 * | 11/2005 | Quake et al. ............... 204/452 |
| 2003/0044781 | A1 | 3/2003 | Korlach et al. |

FOREIGN PATENT DOCUMENTS

| | | |
|---|---|---|
| WO | WO 94/05414 | 3/1994 |
| WO | WO 95/33846 | 12/1995 |
| WO | WO 96/00457 A1 * | 2/1996 |
| WO | WO 96/04547 | 2/1996 |
| WO | WO 97/02357 | 1/1997 |
| WO | WO 97/38200 | 10/1997 |
| WO | WO 98/52691 | 11/1998 |

OTHER PUBLICATIONS

P. J. Crosland-Taylor, Nature (London) 171, 37 (1953).
L. A. Kamensky, M. R. Melamed, H. Derman, Science 150, 630 (1965).
M.A. Van Dilla, T.T. Trujillo, P.F. Mullaney Science 163, 1213 (1969).
Ballantyne, J. P., et al., J. Vac. Sci. Technol. 10:1094 (1974).
M.J. Fulwyer, Science 156, 910 (1974).
Angell et al., Scientific American 248: 44-55 (1983).
T.N. Buican, M. J. Smyth, H. A. Verissman, Applied Optics 26, 5311 (1987).
A. Ashkin, J. M. Dziedzic, Science 235, 1517 (1987).
A. Ashkin, J. M. Dziedzic, Nature 330, 769 (1987).
Manz et al., Trends in Analytical Chemistry 10: 144-149 (1991).
W. D. Volkmuth, et al., DNA Electrophoresis in microlithographic arrays, Letters to Nature vol. 358, Aug. 13, 1992, p. 600-602 (1992).
Castro, A., et al., Anal. Chem. 85: 849-852 (1993).
Harrison, D. J. et al., Science, 261: 895 (1993).
Goodwin, P.M., et al., Nucleic Acids Research 21 (4): 803-806 (1993).
Stemmer, W. P. C. Nature, 370, 389 (1994).
Petty, Jeffery T., et al., Characterization of DNA Size Determination of Small Fragments by Flow Cytometry, Anal. Chemistry 67, 1755-1761 (1995).
Caplus abstract of Kawazumi et al. ("Laser Fluorometry using a visible semiconductor laser and an avalanche photodiode for capillary electrophoresis," Analytical Sciences (1995), 11(4), 587-90).
Hanes, J. & Pluckthun A. Proc. Natl. Acad. Sci., USA 94, 4937 (1997).
Li. P. H. et al., Analytical Chemistry 69, 1564 (1997).
Roberts, R. W. & Szostak, J. W. Proc. Natl. Acad. Sci. USA 94, 12297-12302 (1997).
S. Fiedler, et al. Analytical Chemistry 70, 1909-1915 (1998).
Tawfik, D. and Girffiths, A. Nat. Biotechnol. 16, 652-656 (1998).
J. P. Nolan, L. A. Sklar, Nature Biotechnology 16, 633 (1998).
Jermutus, L., L. A. Ryabova & A. Pluckthun, Curr. Opin. Biotechnol. 9, 534-548 (1998).
L. A. Sklar, Proc. SPIE 3256, 144 (1998).
M. U. Kopp et al., Science, 280: 1046 (1998).
F. H. Arnold, Acct. Chem. Research 31, 125-131 (1998).
Y. Xia et al., Angewandte Chemie International Edition 37, 550 (1998).
Bein, Thomas, efficient Assays for Combinatorial Methods for the Discovery of Catalysts, Angew. Chem. Int. Ed. 38:3, 323-26 (1999).
J. Affholter and F. Arnold, "Engineering a Revolution," Chemistry in Britain, Apr. 1999, p. 48.
Chou, Hou-Pu et al., "A Microfabricated Device For Sizing And Sorting DNA Molecules," Proc. Natl. Acad. Sci., vol. 96, pp. 11-13, Jan. 1999.
Hoffmuller, Ulrich et al., "In Vitro Evolution And Selection of Proteins: Ribosome Display For Larger Libraries," Angew. Chem. Int. Ed., vol. 37, No. 23, pp. 3241-3243, 1998.
Krutenat, R. C., "Metallic Coatings (Survey)," Kirk-Othmer Encyclopedia of Chemical Technology, John Wiley & Sons, Inc., 3rd Edition, vol. 15, pp. 2 cover, 241-274 (1981).
Sweet, Richard G., *Flow Cytometry and Sorting*, John Wiley & Sons, Inc., pp. 5 cover, 177-189, 1979, "Chapter 9—Flow Sorters For Biologic Cells".
Thompson, L. F. et al., "Introduction To Microlithography," 185th Meeting of the American Chemical Society, Seattle, WA, pp. 2 cover pages, 1-13, Mar. 20-25, 1983.
Van Dilla, Marvin A. et al., *Flow Cytometry and Sorting*, John Wiley & Sons, Inc., pp. 5 cover, 11-37, 1979, "Chapter 2—Introduction And Resume of Flow Cytometry And Sorting".

* cited by examiner develop and rinse 1. etch SiO$_2$
2. remove resist etch Si

METHOD AND APPARATUS FOR ANALYSIS AND SORTING OF POLYNUCLEOTIDES BASED ON SIZE

CROSS-REFERENCE TO RELATED APPLICATIONS

This application is a continuation of U.S. patent application Ser. No. 10/021,850, filed Dec. 13, 2001, now U.S. Pat. No. 6,964,736, which is a continuation of U.S. patent application Ser. No. 09/499,943, filed Feb. 8, 2000, now U.S. Pat. No. 6,344,325, which is a continuation of U.S. patent application Ser. No. 08/932,774, filed Sep. 23, 1997, now U.S. Pat. No. 6,221,654, which claims the benefit of U.S. Provisional Application No. 60/026,693, filed Sep. 25, 1996, incorporated herein by reference in its entirety.

STATEMENT AS TO RIGHTS TO INVENTIONS MADE UNDER FEDERALLY SPONSORED RESEARCH AND DEVELOPMENT

This invention was made with government support under Grant Nos. DAAH04-96-1-0141 awarded by the Army Research Office. The government has certain rights in the invention.

FIELD OF THE INVENTION

The present invention relates in general to a method of analyzing and sorting polynucleotides (e.g., DNA) by size. In particular, the invention relates to a method of analyzing and/or sorting individual polynucleotide molecules in a microfabricated device by measuring the signal of an optically-detectable (e.g., fluorescent) reporter associated with the molecules.

REFERENCES

Aine, H. E., et al., U.S. Pat. No. 4,585,209 (1986).
Baker, D. R., in CAPILLARY ELECTROPHORESIS, John Wiley & Sons, New York, 1995.
Ballantyne, J. P., et al., *J. Vac. Sci. Technol.* 10:1094 (1973).
Castro, A., et al., *Anal. Chem.* 85:849-852 (1993).
Goodwin, P. M., et al., *Nucleic Acids Research* 21-(4):803-806 (1993).
Gravesen, P., et al., U.S. Pat. No. 5,452,878 (1995).
Haugland, R. P., in HANDBOOK OF FLUORESCENT PROBES AND RESEARCH CHEMICALS, 5th Ed., Molecular Probes, Inc., Eugene, Oreg. (1992).
Keller, R. A., et al., GB Patent No. 2,264,296 (10/95).
Krutenat, R. C., in KIRK-OTHMER ENCYCLOPEDIA OF CHEMICAL TECHNOLOGY, 3rd Ed., John Wiley & Sons, New York, Vol. 15, 241-274.
O'Connor, J. M., U.S. Pat. No. 4,581,624 (1986).
van Lintel, H. T. G., U.S. Pat. No. 5,271,274 (1993).
Wise, K. D., et al., U.S. Pat. No. 5,417,235 (1995).

BACKGROUND OF THE INVENTION

Identification and separation of nucleic acid fragments by size, such as in sequencing of DNA or RNA, is a widely used technique in many fields, including molecular biology, biotechnology, and medical diagnostics. The most frequently used method for such separation is gel electrophoresis, in which different sized charged molecules are separated by their different rates of movement through a stationary gel under the influence of an electric current. Gel electrophoresis presents several disadvantages, however. The process can be time consuming, and resolution is typically about 10%. Efficiency and resolution decrease as the size of fragments increases; molecules larger than 40,000 are difficult to process, and those larger than 10 million base pairs cannot be distinguished.

Methods have been proposed for determination of the size of nucleic acid molecules based on the level of fluorescence emitted from molecules treated with a fluorescent dye (Keller, et al., 1995; Goodwin, et al., 1993; Castro, et al., 1993). Castro describes the detection of individual molecules in samples containing either uniformly sized (48 Kbp) DNA molecules or a predetermined 1:1 ratio of molecules of two different sizes (48 Kbp and 24 Kbp). A resolution of approximately 12-15% was achieved between these two sizes. There is no discussion of sorting or isolating the differently sized molecules.

In order to provide a small diameter sample stream, Castro uses a "sheath flow" technique wherein a sheath fluid hydrodynamically focuses the sample stream from 100 µm to 20 µm. This method requires that the radiation exciting the dye molecules, and the emitted fluorescence, must traverse the sheath fluid, leading to poor light collection efficiency and resolution problems caused by lack of uniformity. Specifically, this method results in a relatively poor signal-to-noise ratio of the collected fluorescence, leading to inaccuracies in the sizing of the DNA molecules.

Goodwin mentions the sorting of fluorescently stained DNA molecules by flow cytometry. This method, however, employs costly and cumbersome equipment, and requires atomization of the nucleic acid solution into droplets, with the requirement that each droplet contains at most one analyte molecule. Furthermore, the flow velocities required for successful sorting of DNA fragments were determined to be considerably slower than used in conventional flow cytometry, so the method would require adaptations to conventional equipment. Sorting a usable amount (e.g., 100 ng) of DNA using such equipment would take weeks, if not months, for a single run, and would generate inordinately large volumes of DNA solution requiring additional concentration and/or precipitation steps.

It is thus desirable to provide a method of rapidly analyzing and sorting differently sized nucleic acid molecules with high resolution, using simple and inexpensive equipment. A short optical path length is desirable to reduce distortion and improve signal-to-noise of detected radiation. Ideally, sorting of fragments can be carried out using any size-based criteria.

SUMMARY OF THE INVENTION

In one aspect, the present invention includes a microfabricated device for sorting reporter-labelled polynucleotides or polynucleotide molecules by size. The device includes a chip having a substrate into which is microfabricated at least one analysis unit. Each analysis unit includes a main channel, having at one end a sample inlet, having along its length a detection region, and having, adjacent and downstream of the detection region, a branch point discrimination region. The analysis unit further includes a plurality of branch channels originating at the discrimination region and in communication with the main channel, a means for passing a continuous stream of solution containing the molecules through said detection region, such that on average only one molecule occupies the detection region at any given time, a means for measuring the level of reporter from each molecule within the detection region, and a means for directing the molecule to a selected branch channel based on the level of reporter.

In one general embodiment, the directing or sorting means includes a pair of electrodes effective to apply an electric field across the discrimination region, where the applied field is effective to direct a particular molecule into a selected branch channel based on the amount of reporter signal detected from that molecule.

In another general embodiment, a flow of molecules is maintained through the device via a pump or pressure differential, and the directing means comprises a valve structure at the branch point effective to permit the molecule to enter only one of the branch channels.

In still another general embodiment, a flow of molecules is maintained through the device via a pump or pressure differential, and the directing means comprises, for each branch channel, a valve structure downstream of the branch point effective to allow or curtail flow through the channel.

In a related general embodiment, a flow of molecules is maintained through the device via a pump or pressure differential, and the directing means comprises, for each branch channel, a pressure adjusting means at the outlet of each branch channel effective to allow or curtail flow through the channel.

A device which contains a plurality of analysis units may further include a plurality of manifolds, the number of such manifolds typically being equal to the number of branch channels in one analysis unit, to facilitate collection of molecules from corresponding branch channels of the different analysis units.

In preferred embodiments, the device includes a transparent (e.g., glass) cover slip bonded to the substrate and covering the channels to form the roof of the channels. The channels in the device are preferably between about 1 μm and about 10 μm in width and between about 1 μm and about 10 μm in depth, and the detection region has a volume of between about 1 fl and about 1 pl.

The exciting means may be, for example, an external laser, a diode or integrated semiconductor laser or a high-intensity lamp (e.g., mercury lamp).

The measuring means may be, for example, a fluorescence microscope in connection with an intensified (e.g., SIT) camera, an integrated photodiode, or the like.

In another aspect, the invention includes a method of isolating polynucleotides having a selected size. The method includes A) flowing a continuous stream of solution containing reporter-labeled polynucleotides through a channel comprising a detection region having a selected volume, where the concentration of the molecules in the solution is such that the molecules pass through the detection region one by one, B) determining the size of each molecule as it passes through the detection region by measuring the level of the reporter, C) in the continuous stream of solution, diverting (i) molecules having the selected size into a first branch channel, and (ii) molecules not having the selected size into a second branch channel, and D) collecting polynucleotides diverted into the first branch channel.

In general preferred embodiments, the concentration of polynucleotides in the solution is between about 10 fM and about 1 nM and the detection region volume is between about 1 fl and about 1 pl.

The determining typically includes quantitating an optical signal, such as a fluorescence signal, from an optical reporter, such as a fluorescent moiety, associated with the polynucleotides. Exemplary fluorescent moieties are fluorescent reporters selected from the group consisting of POPO, BOBO, YOYO, and TOTO.

In a general embodiment, the diverting includes the transient application of an electric field effective to bias (i) a molecule having the selected size (e.g., between about 100 bp and about 10 mb) to enter the first branch channel, and (ii) a molecule not having the selected size to enter the second branch channel.

The method may be applied to diverting a molecule having the selected size into the first branch channel, wherein the diverting includes blocking the flow in the second branch channel such that the continuous stream of solution carries the molecule having the selected size into the first branch channel. Alternatively or in addition, the method may be applied for diverting a molecule not having the selected size into the second branch channel, wherein the diverting includes blocking the flow in the first branch channel such that the continuous stream of solution carries the fragment not having the selected size into the second branch channel.

The diverting may include a mechanical switch effective to direct (i) a fragment having the selected size to enter the first branch channel, and (ii) a fragment not having the selected size to enter the second branch channel.

In yet another aspect, the invention includes a method of sizing polynucleotides in solution. This method includes: A) flowing a continuous stream of solution containing reporter-labeled polynucleotides through a microfabricated channel comprising a detection region having a selected volume, where the concentration of the molecules in the solution is such that most molecules pass through the detection region one by one, and B) determining the size of each molecule as it passes through the detection region by measuring the level of the reporter.

In still another aspect, the invention includes a microfabricated device for sorting reporter-labelled cells by the level of reporter they contain. The device includes a chip having a substrate into which is microfabricated at least one analysis unit. Each analysis unit includes a main channel, having at one end a sample inlet, having along its length a detection region, and having, adjacent and downstream of the detection region, a branch point discrimination region. The analysis unit further includes a plurality of branch channels originating at the discrimination region and in communication with the main channel, a means for passing a continuous stream of solution containing the cells through said detection region, such that on average only one cell occupies the detection region at any given time, a means for measuring the level of reporter from each cell within the detection region, and a means for directing the cell to a selected branch channel based on the level of reporter.

In one embodiment, a flow of cells is maintained through the device via a pump or pressure differential, and the directing means comprises a valve structure at the branch point effective to permit each cell to enter only one of the branch channels.

In another general embodiment, a flow of cells is maintained through the device via a pump or pressure differential, and the directing means comprises, for each branch channel, a valve structure downstream of the branch point effective to allow or curtail flow through the channel.

In a related general embodiment, a flow of cells is maintained through the device via a pump or pressure differential, and the directing means comprises, for each branch channel, a pressure adjusting means at the outlet of each branch channel effective to allow or curtail flow through the channel.

A device which contains a plurality of analysis units may further include a plurality of manifolds, the number of such manifolds typically being equal to the number of branch channels in one analysis unit, to facilitate collection of cells from corresponding branch channels of the different analysis units.

In preferred embodiments, the device includes a transparent (e.g., glass) cover slip bonded to the substrate and covering the channels to form the roof of the channels. The channels in the device are preferably between about 20 μm and 500 μm in width and between about 20 μm and 500 μm in depth, and the detection region has a volume of between about 10 pl and 100 nl.

The exciting means may be, for example, an external laser, a diode or integrated semiconductor laser or a high-intensity lamp (e.g., mercury lamp).

The measuring means may be, for example, a fluorescence microscope in connection with an intensified (e.g., SIT) camera, an integrated photodiode, or the like.

In another aspect, the invention includes a method of isolating cells having a selected amount of bound optically-detectable (e.g., fluorescent) reporter. The method includes A) flowing a continuous stream of solution containing reporter-labeled cells through a channel comprising a detection region having a selected volume, where the concentration of the cells in the solution is such that the molecules pass through the detection region one by one, B) determining the amount of reporter on each cell as it passes through the detection region, C) in the continuous stream of solution, diverting (i) cells having the selected amount of reporter into a first branch channel, and (ii) cells not having the selected amount of reporter into a second branch channel, and D) collecting cells diverted into the branch channels.

The method may be applied to diverting a cell having the selected amount of reporter into the first branch channel, wherein the diverting includes blocking the flow in the second branch channel such that the continuous stream of solution carries the cell having the selected amount of reporter into the first branch channel. Alternatively or in addition, the method may be applied for diverting a cell not having the selected amount of reporter into the second branch channel, wherein the diverting includes blocking the flow in the first branch channel such that the continuous stream of solution carries the fragment not having the selected amount of reporter into the second branch channel.

The diverting may include a mechanical switch effective to direct (i) a cell having the selected amount of reporter to enter the first branch channel, and (ii) a cell not having the selected amount of reporter to enter the second branch channel.

The method may be applied to any procaryotic or eukaryotic cells, such as bacterial cells, mammalian cells, and the like. The method is particularly useful for the sorting of mammalian (e.g., human) blood cells, such as peripheral blood mononuclear cells (PBMCs), based on the patterns of expression of various antigens, such as HLA DR, CD3, CD4, CD8, CD11a, CD11c, CD14, CD16, CD20, CD45, CD45RA, CD62L, etc.

DETAILED DESCRIPTION OF THE INVENTION

I. Definitions

The terms below have the following meanings unless indicated otherwise.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

II. Overview of Invention

According to one aspect of the present invention, polynucleotides, e.g., DNA, can be sorted dynamically in a continuous flow stream of microscopic dimensions based on the molecules' molecular weight using a microfabricated polynucleotide sorting device. The polynucleotides, suspended in a suitable carrier fluid (e.g., ddH2O or TE), are introduced into an inlet end of a narrow channel in the sorting device. The molecular weight of each molecule is calculated from the intensity of signal from an optically-detectable reporter incorporated into or associated with the polynucleotide molecule as the molecule passes through a "detection window" or "detection region" in the device. Molecules having a molecular weight falling within a selected range are diverted into an selected output or "branch" channel of the device. The sorted polynucleotide molecules may be collected from the output channels and used in subsequent manipulations.

According to another aspect of the invention, a device such as described above, but not necessarily including components for sorting the molecules, can be used to simply quantitate the size range of polynucleotides in a sample, and store or feed this information into a processor or computer for subsequent analysis or display, e.g., as a size distribution histogram. Such a device enables the generation of the type of polynucleotide fragment length data now commonly obtained from analytical gels, such as agarose or polyacrylamide gels, in a fraction of the time required for preparation and analysis of gels, and using a substantially smaller amount of sample.

According to yet another aspect of the invention, a sorting device such as described above can be used to sort cells based on the level of expression of selected cell markers, such as cell surface markers, in a manner similar to that currently employed using fluorescence-activated cell sorting (FACS) machines.

III. Microfabricated Polynucleotide Sorting Device

Figure 1:
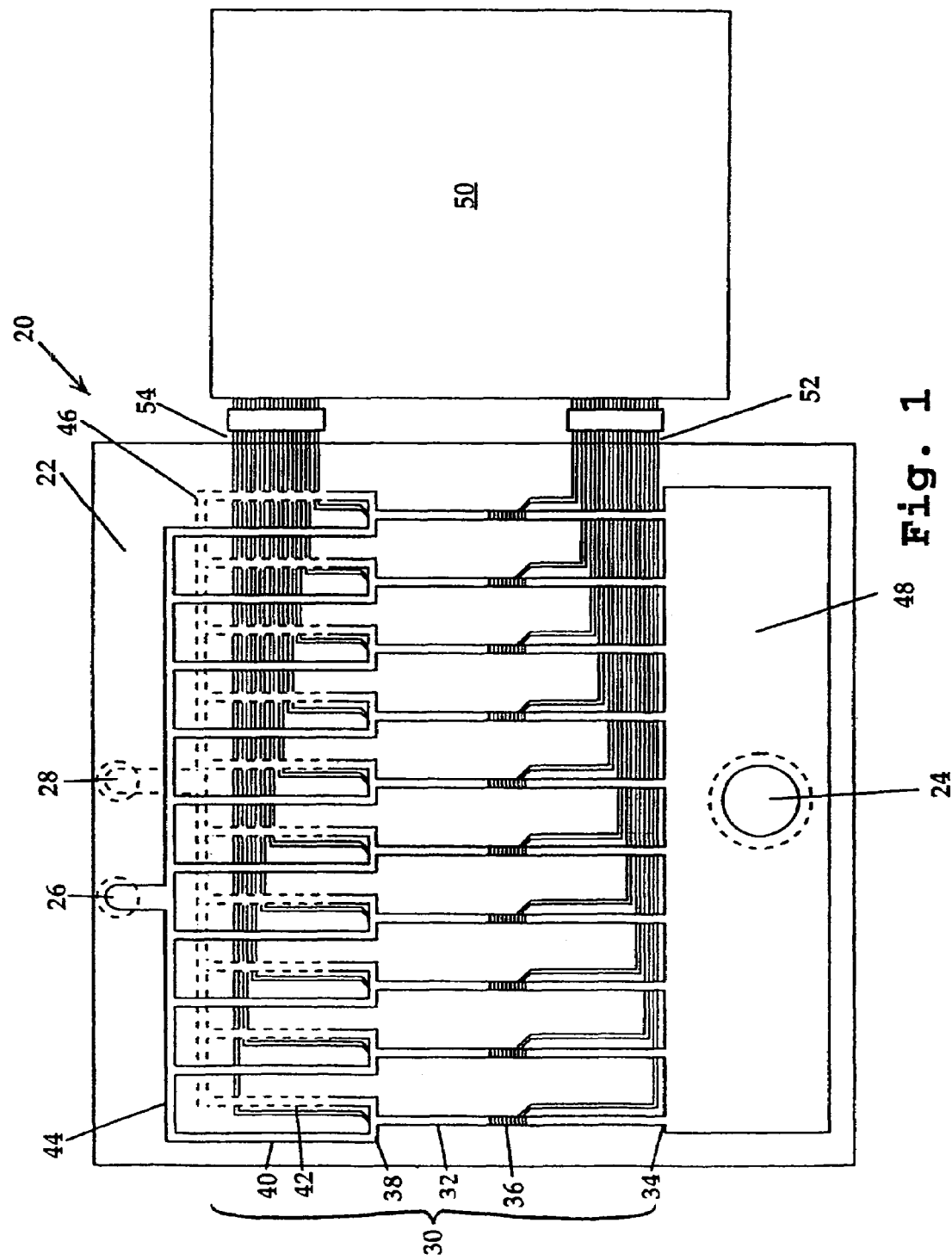
FIG. 1 shows a nucleic acid sorting device in accordance with one embodiment of the invention.

FIG. 1 shows an embodiment of a microfabricated polynucleotide sorting device 20 in accordance with the invention. The device is preferably fabricated from a silicon microchip 22. The dimensions of the chip are those of typical microchips, ranging between about 0.5 cm to about 5 cm per side and about 0.1 mm to about 1 cm in thickness. The device contains a solution inlet 24, two or more solution outlets, such as outlets 26 and 28, and at least one analysis unit, such as the unit at 30.

Each analysis unit includes a main channel 32 having at one end a sample inlet 34, and downstream of the sample inlet, a detection region 36, and downstream of the detection region 36 a discrimination region 38. A plurality of branch channels, such as channels 40 and 42, are in fluid communication with and branch out from the discrimination region. The dimensions of the main and branch channels are typically between about 1 μm and 10 μm per side, but may vary at various points to facilitate analysis, sorting and/or collection of molecules.

In embodiments such as shown in FIG. 1, where the device contains a plurality of analysis units, the device may further contain collection manifolds, such as manifolds 44 and 46, to facilitate collection of sample from corresponding branch channels of different analysis units for routing to the appropriate solution outlet. The manifolds are preferably microfabricated into different levels of the device, as indicated by the dotted line representing manifold 46. Similarly, such embodiments may include a sample solution reservoir, such as reservoir 48, to facilitate introduction of sample into the sample inlet of each analysis unit.

Also included with the device is a processor, such as processor 50. The processor can be integrated into the same chip as contains the analysis unit(s), or it can be separate, e.g., an independent microchip connected to the analysis unit-containing chip via electronic leads, such as leads 52 (connected to the detection region(s) and 54 (connected to the discrimination region(s)).

Figure 2:
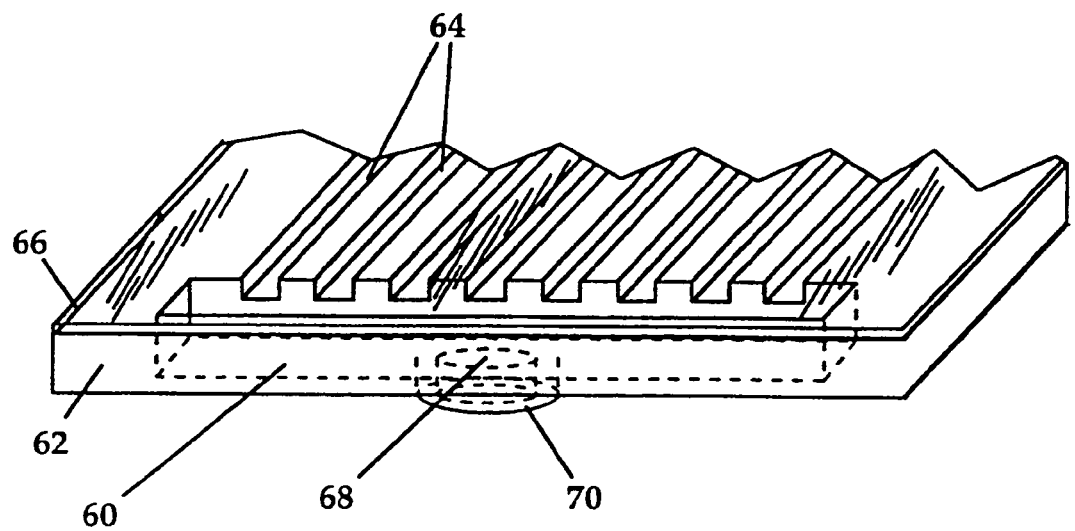
FIG. 2 shows a partial perspective view of a nucleic acid sorting device, showing a sample solution reservoir and sample inlet.

As mentioned above, the device may be microfabricated with a sample solution reservoir to facilitate introduction of a polynucleotide solution into the device and into the sample inlet of each analysis unit. With reference to FIG. 2, the reservoir is microfabricated into the silicon substrate of the chip 62, and is covered, along with the channels (such as main channel 64) of the analysis units, with a glass coverslip 66. The device solution inlet comprises an opening 68 in the floor of the microchip. The inlet may further contain a connector 70 adapted to receive a suitable piece of tubing, such as liquid chromatography or HPLC tubing, through which the sample may be supplied. Such an arrangement facilitates introducing the sample solution under positive pressure, to achieve a desired flow rate through the channels as described below.

Downstream of the sample inlet of the main channel of each analysis unit is the detection region, designed to detect the level of an optically-detectable reporter associated with polynucleotides present in the region. Exemplary embodiments of detection regions in devices of the invention are shown in FIGS. 3A and 3B.

Figure 3A:
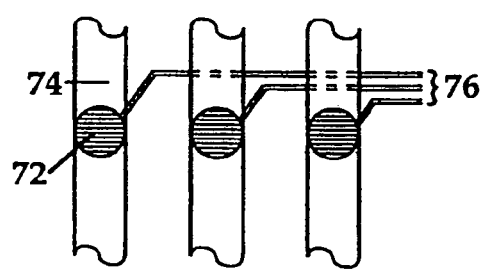
FIG. 3A shows one embodiment of a detection region used in a nucleic acid sorting device, having an integrated photodiode detector.

With reference to FIG. 3A, each detection region is formed of a portion of the main channel of an analysis unit and a photodiode, such as photodiode 72, located in the floor of the main channel. In this embodiment, the area detectable by the detection region is the circular portion each channel defined by the receptive field of the photodiode in that channel. The volume of the detection region is the volume of a cylinder with a diameter equal to the receptive field of the photodiode and a height equal to the depth of the channel above the photodiode.

The signals from the photodiodes are carried via output lines 76 to the processor (not shown in FIGS. 3A and 3B), which processes the signals into values corresponding to the length of the polynucleotide giving rise to the signal. The processor then uses this information to control active elements in the discrimination region.

Figure 3B:
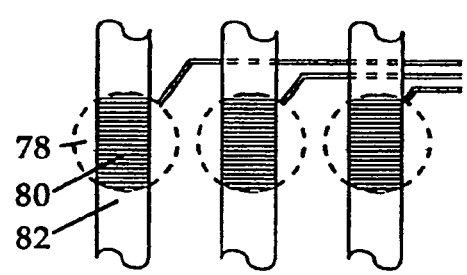
FIG. 3B shows another embodiment of a detection region, having an integrated photodiode detector, and providing a larger detection volume (than the embodiment of FIG. 3A)

With reference to FIG. 3B, the photodiode 78 can be larger in diameter than the width of the main channel, forming a detection region 80 that is longer (along the length of the main channel 82) than it is wide. The volume of such a detection region is approximately equal to the cross-sectional area of the channel above the diode multiplied by the diameter of the diode.

The detection region is connected by the main channel to the discrimination region. The discrimination region may be located immediately downstream of the detection region, or may be separated by a suitable length of channel. Constraints on the length of channel between the detection and discrimination regions are discussed below, with respect to the operation of the device. This length is typically between about 1 μm and about 2 cm.

The discrimination region is at the junction of the main channel and the branch channels. It comprises the physical location where molecules are directed into a selected branch channel. The means by which the molecules are directed into a selected branch channel may (i) be present in the discrimination region, as in, e.g., electrophoretic or microvalve-based discrimination, or (ii) be present at a distant location, as in, e.g., electroosmotic or flow stoppage-based discrimination. The following paragraphs illustrate examples of discrimination regions employing such discrimination means.

Figure 4B:
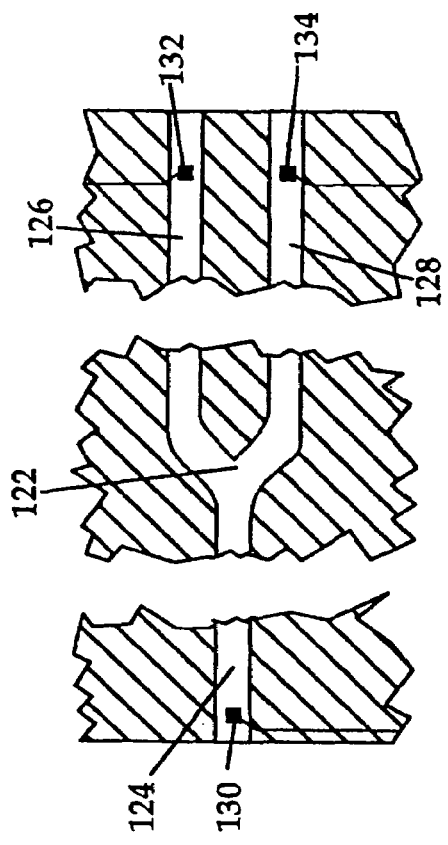
FIG. 4B shows another embodiment of a discrimination region used in a nucleic acid sorting device, having electrodes disposed for electroosmotic discrimination.
Figure 4D:
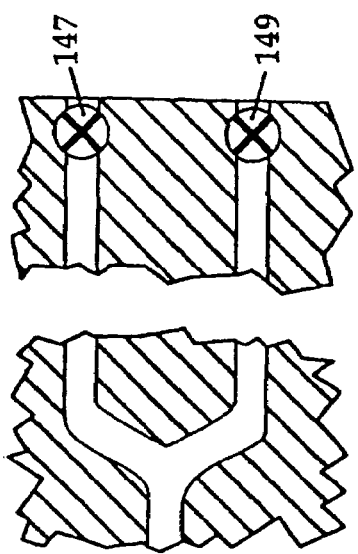
FIGS. 4C and 4D show two further embodiments of a discrimination region, having valves disposed for pressure electrophoretic separation, where the valves are within the branch point, as shown in 4C, or within the branch channels, as shown in 4D.
Figure 4A:
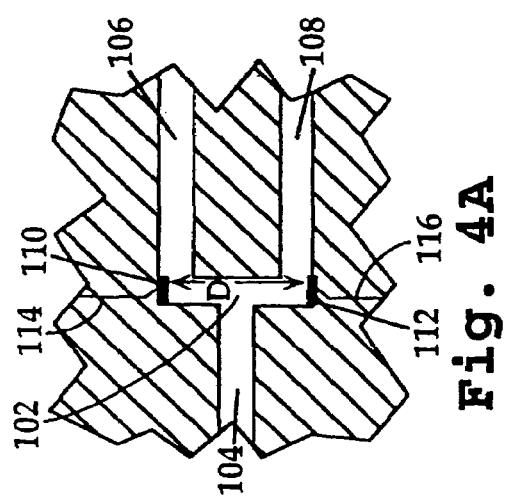
FIG. 4A shows one embodiment of a discrimination region used in a nucleic acid sorting device, having electrodes disposed within the channels for electrophoretic discrimination.

FIG. 4A shows an electrophoretic discrimination means, with a discrimination region 102 at the junction of the main channel 104 and two branch channels 106 and 108. The region includes electrodes 110 and 112 connected to leads 114 and 116, which are in turn connected to a voltage source (not shown) incorporated into or controlled by the processor (not shown). The distance between the electrodes is preferably less than the average distance between molecules in the main channel. The dimensions of the electrodes are typically on the same order as the dimensions of the channels in which they are positioned.

Electroosmotic discrimination, as is described more fully with respect to the operation of the device, below, is preferably employed with analysis units having only two branch channels. FIG. 4B shows a discrimination region 122 at the junction of the main channel 124 and two branch channels 126 and 128. The discrimination means includes an electrode at the sample inlet of the main channel, such as electrode 130, and electrodes at the sample outlets of the branch channels, such as electrodes 132 and 134.

Figure 4C:
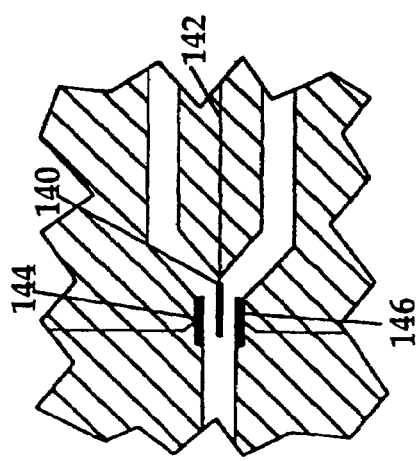
Figure 5A:
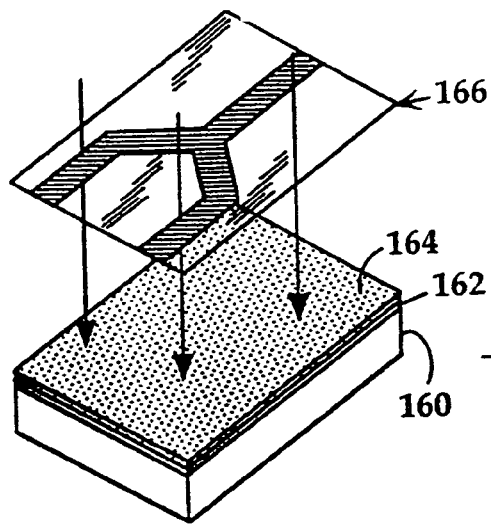
FIGS. 5A-5D show initial steps in photolithographic microfabrication of a nucleic acid sorting device from a silicon wafer, using photolithography and several stages of etching.
Figure 5B:
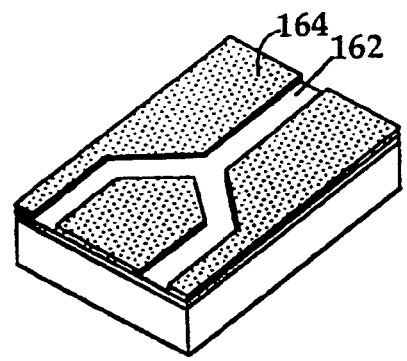
Figure 5C:
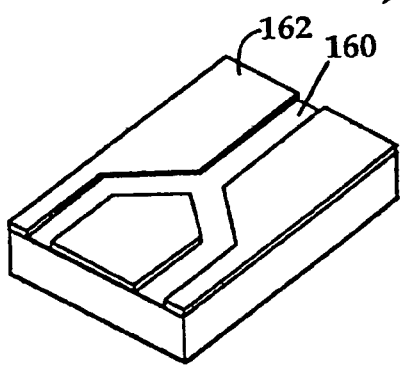
Figure 5D:
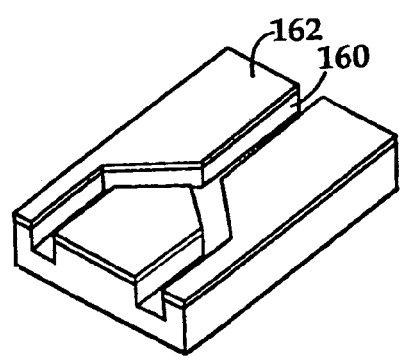

In another embodiment of the invention, the polynucleotides are directed into a selected branch channel via a valve in the discrimination region. An exemplary valve is shown in FIG. 4C. The valve consists of a thin extension of material 140 to which a charge can be applied via electrode lead 142. The extension 140 can then be deflected to close one or the other of the branch channels by application of a voltage across electrodes 144 and 146.

FIG. 4D shows an embodiment employing flow stoppage in one or more branch channels as a discrimination means. The sample solution is moved through such a device by application of positive pressure at the solution inlet. Discrimination or routing of the polynucleotide molecules is affected by simply blocking branch channels or branch channel sample outlets into which the sample is not supposed to go, and leaving a single selected outlet open.

IV. Microfabricated Polynucleotide Analysis Device

Also included in the present invention is a microfabricated polynucleotide analysis device, suitable for quantitation and analysis of the size distribution of polynuclebtide fragments in solution. Such a device is a simplified version of the sorting device described above, in that analysis units in the device do not contain a discrimination region or branch channels, and the device does not contain a means for directing molecules to selected branch channels. Each analysis unit comprises a single main channel containing a detection region as described above.

Since the optics which collect the optical signal (e.g., fluorescence) can be situated immediately adjacent the flow stream (e.g., diode embedded in the channel of a microscope objective adjacent a glass coverslip covering the channel), the signal-to-noise ratio of the signal collected using a microfabricated polynucleotide analysis device of the invention is high relative to other types of devices. Specifically, the present methods allow, e.g., the use of oil-immersion high numerical apperature (N.A.) microscope objectives to collect the light (e.g., 1.4 N.A.). Since the collection of light is proportional to the square of the N.A., a 1.4 N.A. objective provides about a four-fold better signal than an 0.8 N.A. objective.

V. Microfabricated Cell Sorting Device

The present invention also includes a microfabricated device for sorting reporter-labelled cells by the level of reporter they contain. The device is similar to polynucleotide-sorting device described above, but is adapted for handling particles on the size scale of cells rather than molecules. This difference is manifested mainly in the dimensions of the microfabricated channels, detection and discrimination regions. Specifically, the channels in the device are typically between about 20 μm and about 500 μm in width and between about 20 μm and about 500 μm in depth, to allow for an orderly flow of cells in the channels. Similarly, the volume of the detection region in a cell sorting device is larger than that of the polynucleotide-sorting device, typically being in the range of between about 10 pl and 100 nl.

To prevent the cells from adhering to the sides of the channels, the channels (and coverslip) preferably contain a coating which minimizes cell adhesion. Such a coating may be intrinsic to the material from which the device is manufactured, or it may be applied after the structural aspects of the channels have been microfabricated. An exemplary coating has the surface properties of a material such as "TEFLON".

The device may be used to sort any procaryotic (e.g., bacterial) or eukaryotic (e.g., mammalian) cells which can be labeled (e.g., via antibodies) with optically-detectable reporter molecules (e.g., fluorescent dyes). Exemplary mammalian cells include human blood cells, such as human peripheral blood mononuclear cells (PBMCs). The cells can be labeled with antibodies directed against any of a variety of cell marker antigens (e.g., HLA DR, CD3, CD4, CD8, CD11a, CD11c, CD14, CD16, CD20, CD45, CD45RA, CD62L, etc.), and the antibodies can in turn be detected using an optically-detectable reporter (either via directly-conjugated reporters or via labelled secondary antibodies) according to methods known in the art.

Figure 7:
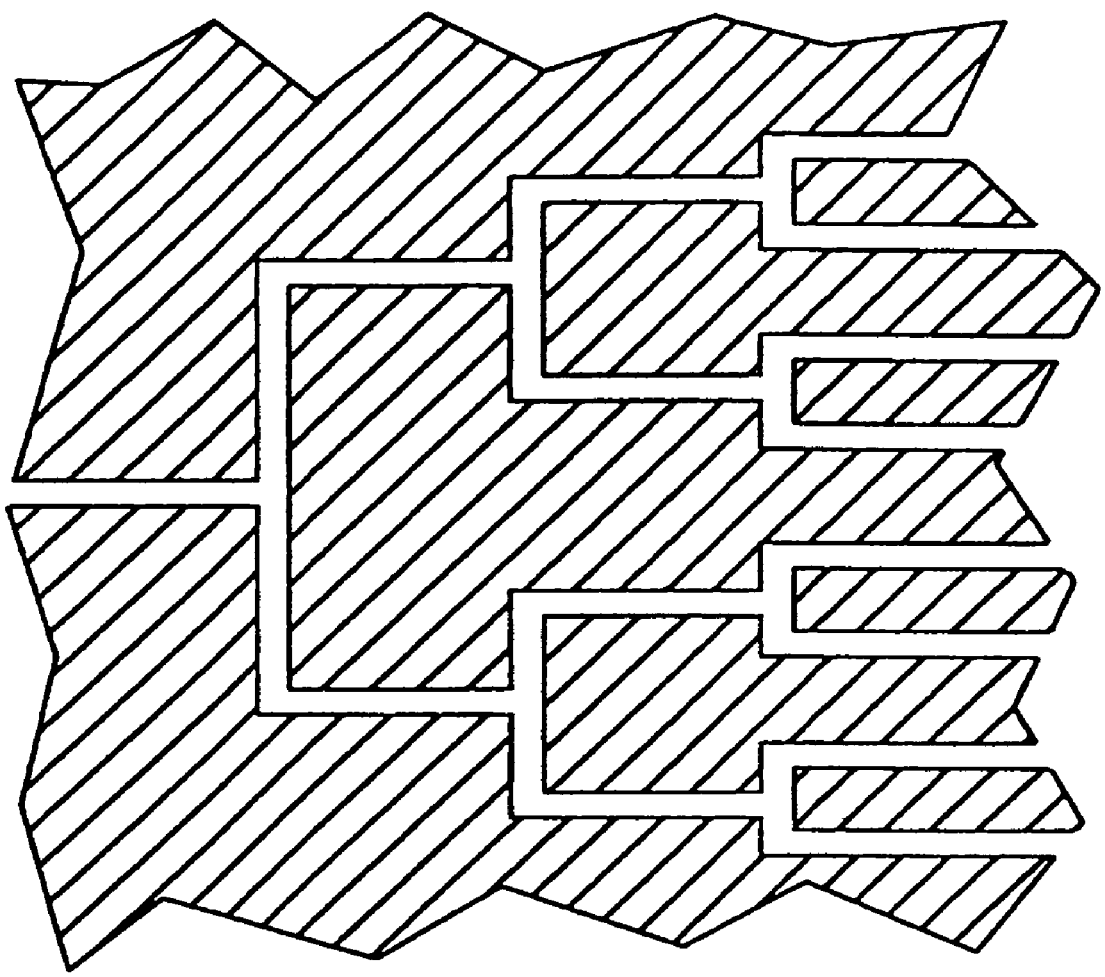
FIG. 7 shows a device with analysis units containing a cascade of detection and discrimination regions suitable for successive rounds of polynucleotide or cell sorting.

It will be appreciated that the cell sorting device and method described above can be used simultaneously with multiple optically-detectable reporters having distinct optical properties. For example, the fluorescent dyes fluorescein (FITC), phycoerythrin (PE), and "CYCHROME" (Cy5-PE) can be used simultaneously due to their different excitation and emission spectra. The different dyes may be assayed, for example, at successive detection and discrimination regions. Such regions may be cascaded as shown in FIG. 7 to provide samples of cells having a selected amount of signal from each dye.

VI. Operation of a Microfabricated Polynucleotide Sorting Device

In operation of the device, a solution of reporter-labelled polynucleotides is prepared as described below and introduced into the sample inlet end(s) of the analysis unit(s). The solution may be conveniently introduced into a reservoir, such as reservoir 48 of FIG. 1, via a port or connector, such as connector 70 in FIG. 2, adapted for attachment to a segment of tubing, such as liquid chromatography or HPLC tubing.

It is typically advantageous to "hydrate" the device (i.e., fill the channels of the device with the solvent, e.g., water or a buffer solution, in which the polynucleotides will be suspended) prior to introducing the polynucleotide-containing solution. Such hydrating can be achieved by supplying water or the buffer solution to the device reservoir and applying hydrostatic pressure to force the fluid through the analysis unit(s).

Following such hydration, the polynucleotide-containing solution is introduced into the sample inlets of the analysis unit(s) of the device. As the stream of polynucleotides derivatized with a detectable reporter (e.g., a fluorescent dye) is passed in a single file manner through the detection region, the optical signal (e.g., fluorescence) from the optically-detectable reporter moieties on each molecule are quantitated by an optical detector and converted into a number used in calculating the approximate length of polynucleotide in the detection region.

Exemplary reporter moieties, described below in reference to sample preparation, include fluorescent moieties which can be excited to emit light of characteristic wavelengths by an excitation light source. Fluorescent moieties have an advantage in that each molecule can emit a large number of photons (e.g., upward of $10^6$) in response to exciting radiation. Suitable light sources include lasers, laser diodes, high-intensity lamps, e.g., mercury lamps, and the like. In embodiments where a lamp is used, the channels are preferably shielded from the light in all regions except the detection region, to avoid bleaching of the label. In embodiments where a laser is used, the laser can be set to scan across a set of detection regions from different analysis units.

Where laser diodes are used as a light source, the diodes may be microfabricated into the same chip that contains the analysis units (polynucleotide analysis chip; PAC). Alternatively, the laser diodes may be incorporated into a second chip (laser diode chip; LDC) that is placed adjacent the PAC such that the laser light from the diodes shines on the detection regions. The photodiodes in the LDC are preferably placed at a spacing that corresponds to the spacing of the detection regions in the PAC.

Other optically-detectable reporter moieties include chemiluminescent moieties, which can be used without an excitation light source.

The level of reporter signal is measured using an optical detector, such as a photodiode (e.g., an avalanche photodiode), a fiber-optic light guide leading, e.g., to a photomultiplier tube, a microscope with a high numerical apperature (N.A.) objective and an intensified video camera, such as a SIT camera, or the like. The detector may be microfabricated or placed into the PAC itself (e.g., a photodiode as illustrated in FIGS. 3A and 3B), or it may be a separate element, such as a microscope objective.

In cases where the optical detector is a separate element, it is generally necessary to provide a means to restrict the collection of signal from the detection region of a single analysis unit. It may also be advantageous to provide an automated means of scanning or moving the detector relative to the PAC. For example, the PAC can be secured in a movable mount (e.g., a motorized/computer-controlled micromanipulator) and scanned under the objective. A fluorescence microscope, which has the advantage of a built-in excitation light source (epifluorescence), is preferably employed for detection of a fluorescent reporter.

Since current microfabrication technology enables the creation of sub-micron structures employing the elements described herein, the dimensions of the detection region are influenced primarily by the size of the molecules under study. These molecules can be rather large by molecular standards. For example, lambda DNA (~50 kb) in solution has a diameter of approximately 0.5 µm. Accordingly, detection regions used for detecting polynucleotides in this size range have a cross-sectional area large enough to allow such a molecule to pass through without being substantially slowed down relative to the flow of the solution carrying it and causing a "bottle neck". The dimensions of a channel should therefore be at least about twice, preferably at least about five times as large per side or in diameter as the diameter of the largest molecule that will be passing through it.

Another factor important to consider in the practice of the present invention is the optimal concentration of polynucleotides in the sample solution. The concentration should be dilute enough so that a large majority of the polynucleotide molecules pass through the detection region one by one, with only a small statistical chance that two or more molecules pass through the region simultaneously. This is to insure that for the large majority of measurements, the level of reporter measured in the detection region corresponds to a single molecule, rather than two individual molecules.

The parameters which govern this relationship are the volume of the detection region and the concentration of molecules in the sample solution. The probability that the detection region will contain two or more molecules ($P_{\geq 2}$) can be expressed as $$P_{\geq 2} = 1 - \{1+[DNA]*V\} * e^{-[DNA] \cdot V}$$

where [DNA] is the concentration of polynucleotides in units of molecules per $\mu m^3$ and V is the volume of the detection region in units of $\mu m^3$.

It will be appreciated that $P_{\geq 2}$ can be minimized by decreasing the concentration of polynucleotides in the sample solution. However, decreasing the concentration of polynucleotides in the sample solution also results in increased volume of solution processed through the device and can result in longer run times. Accordingly, the objectives of minimizing the simultaneous presence of multiple molecules in the detection chamber (to increase the accuracy of the sorting) needs to be balanced with the objective of generating a sorted sample in a reasonable time in a reasonable volume containing an acceptable concentration of polynucleotide molecules.

The maximum tolerable $P_{\geq 2}$ depends on the desired "purity" of the sorted sample. The "purity" in this case refers to the fraction of sorted polynucleotides that are in the specified size range, and is inversely proportional to $P_{\geq 2}$.

For example, in applications where high purity is not required, such as the purification of a particular restriction fragment from an enzymatic digest of a portion of vector DNA, a relatively high $P_{\geq 2}$ (e.g., $P_{\geq 2}$=0.2) may be acceptable. For most applications, maintaining $P_{\geq 2}$ at or below about 0.1 provides satisfactory results.

In an example where $P_{\geq 2}$ is equal 0.1, it is expected that in about 10% of measurements, the signal from the detection region will be due to the presence of two or more polynucleotide molecules. If the total signal from these molecules is in the range corresponding to the desired size fragment, these (smaller) molecules will be sorted into the channel or tube containing the desired size fragments.

The DNA concentration needed to achieve a particular value $P_{\geq 2}$ in a particular detection volume can be calculated from the above equation. For example, a detection region in the shape of a cube 1 µm per side has a volume of 1 femtoliter (fl). A concentration of molecules resulting, on average, in one molecule per fl, is about 1.7 nM. Using a $P_{\geq 2}$ value of about 0.1, the polynucleotide concentration in a sample analyzed or processed using such a 1 fl detection region volume is approximately 0.85 nM, or roughly one DNA molecule per 2 detection volumes ([DNA]*V=~0.5). If the concentration of DNA is such that [DNA]*V is 0.1, $P_{\geq 2}$ is less than 0.005; i.e., there is less than a one half of one percent chance that the detection region will at any given time contain two of more fragments.

The signal from the optical detector is routed, e.g., via electrical traces and pins on the chip, to a processor, which processes the signals into values corresponding to the length of the polynucleotide giving rise to the signal. These values are then compared, by the processor, to pre-loaded instructions containing information on which branch channel molecules of a particular size range will be routed into. Following a delay period that allows the molecule from which the reporter signal originated to arrive at the discrimination region, the processor sends a signal to actuate the active elements in the discrimination region such that the molecule is routed into the appropriate branch channel.

The delay period is determined by the rate at which the molecules move through the channel (their velocity relative to the walls of the channel) and the length of the channel between the detection region and the discrimination region. In cases where the sample solution is moved through the device using hydrostatic pressure (applied, e.g., as pressure at the inlet end and/or suction at the outlet end), the velocity is typically the flow rate of the solution. In cases where the molecules are pulled through the device using some other means, such as via electroosmotic flow with an electric field set up between the inlet end and the outlet end, the velocity as a function of molecule size can be determined empirically by running standards, and the velocity for a specific molecule calculated based on the size calculated for it from the reporter signal measurement.

A relevant consideration with respect to the velocity at which the polynucleotide molecules move through the device is the shear force that they may be subject to. At the channel dimensions contemplated herein, the flow through the channels of the device is primarily laminar flow with an approximately parabolic velocity profile. Since the cross-sectional area of the channels in the device can be on the same order of magnitude as the diameter of the molecules being analyzed, situations may arise where a portion of a particular molecule is very near the wall of the channel, and is therefore in a low-velocity region, while another portion of the molecule is near the center of the channel, i.e., in a high-velocity region. This situation creates a shear force (F) on the molecule, which can be estimated using the following expression:

$$F = 6\pi\eta R_\lambda V$$

where $R_\lambda$ is the radius of the molecule and $\eta$ is the viscosity of the solution. This expression assumes that the molecule is immobilized on a stationary surface and subject to uniform flow of velocity V.

The amount of force necessary to break a double-stranded fragment of DNA is approximately 100 pN. Accordingly, the maximal shear force that the molecules are subjected to should preferably be kept below this value. Substituting appropriate values for the variables in the above expression for lambda DNA yields a maximum velocity of about 1 cm/sec for a channel 1 μm in radius (i.e., a channel of a dimension where one portion of the lambda molecule can be at or near the wall of the channel with the opposite side in the center of the channel). Since devices designed for use with such large molecules will typically have channels that are considerably larger in diameter, the maximum "safe" velocity will typically be greater than 1 cm/sec.

As discussed above, the sample solution introduced into a device of the invention should be dilute enough such that there is a high likelihood that only a single molecule occupies the detection region at any given time. It follows then that as the solution flows through the device between the detection and discrimination regions, the molecules will be in "single file" separated by stretches of polynucleotide-free solution. The length of the channel between the detection and discrimination region should therefore not be so long as to allow random thermal diffusion to substantially alter the spacing between the molecules. In particular, the length should be short enough that it can be traversed in a time short enough such that even the smallest molecules being analyzed will typically not be able to diffuse and "switch places" in the line of molecules.

The diffusion constant of a 1 kb molecule is approximately 5 $\mu m^2$/sec; the diffusion equation gives the distance that the molecule diffuses in time t as:

$$<x^2> \sim Dt$$

Using this relationship, it can be appreciated that a 1 kbp fragment takes about 0.2 seconds to diffuse 1 μm. The average spacing of molecules in the channel is a function of the cross-sectional area of the channel and the molecule concentration, the latter being typically determined in view of acceptable values of $P_{\geq 2}$ (see above). From the above relationships, it is then straightforward to calculate the maximum channel length between the detection and discrimination region which would ensure that molecules don't "switch places". In practice, the channel length between the detection and discrimination regions is between about 1 μm and about 2 cm.

As illustrated above with respect to FIGS. 4A, 4B 4C and 4D, there are a number of ways in which molecules can be routed or sorted into a selected branch channel. For example, in a device employing the discrimination region shown in FIG. 4A, the solution is preferably moved through the device by hydrostatic pressure. Absent any field applied across electrodes 110 and 112, a molecule would have an equal probability of entering one or the other of the two branch channels 106 and 108. The sorting is accomplished by the processor temporarily activating a voltage source connected to the electrode leads 114 and 116 just before or at the time the molecule to be routed enters the junction of the main channel and the two branch channels. The resulting electric field exerts a force on the negatively-charged DNA molecule, biasing it toward the positively-charged electrode. The molecule will then be carried down the branch channel containing the positively-charged electrode by the bulk solution flow. The electric field is turned off when the molecule has committed itself to the selected channel. As soon as the molecule clears the corner from the discrimination region and into the branch channel, it escapes effects of the electric field that will be applied to the next molecule in the solution stream.

The discrimination region shown in FIG. 4B is designed for use in a device that employs electroosmotic flow, rather than flow induced by hydrostatic pressure, to move both the polynucleotides and bulk solution through the device. Electrodes are set up in the channels at the inlet and outlet ends of the device. Application of an electric field at the ends of the channels (with electrode 130 being negative, and electrodes 132 and 134 being positive) sets up bulk solution flow according to well-established principles of electroosmotic flow (see, e.g., Baker, 1995). When a specific polynucleotide molecule enters the junction region between the main channel and the two branch channels, the voltage to one of either electrodes 132 or 134 is shut off, leaving a single attractive force, acting on the solution and the DNA molecule, into the selected branch channel. As above, both branch channel electrodes are activated after the molecule has committed to the selected branch channel in order to continue bulk flow through both channels.

In another embodiment of the invention, shown in FIG. 4C, the polynucleotides are directed into a selected branch channel via a valve in the discrimination region. An exemplary valve is shown in FIG. 4C. The valve consists of a thin extension of material 140 which can be charged via an electrode 142. The extension can then be deflected to close one or the other of the branch channels by application of an appropriate voltage across electrodes 144 and 146. As above, once the molecule has committed, the voltage can be turned off.

In a device in which the sample solution is moved through the device by application of positive pressure at the sample inlet end(s) of the analysis unit(s), the discrimination function may be affected by simply blocking branch channel sample outlets into which the sample is not supposed to go, and leaving the selected outlet open. Due to the small size scale of the channels and the incompressibility of liquids, blocking the solution flow creates an effective "plug" in the unselected branch channels, routing the molecule along with the bulk solution flow into the selected channel. This embodiment is illustrated in FIG. 4D. It can be achieved by, for example, incorporating valve structures downstream of the discrimination region.

Alternatively, the discrimination function may be affected by changing the hydrostatic pressure at the sample outlets of the branch channels into which the sample is not supposed to go. Specifically, if the branch channels in a particular analysis unit all offer the same resistance to fluid flow, and the pressure at the sample inlet of the main channel of an analysis unit is P, then the fluid flow out of any selected branch channel can be stopped by applying a pressure P/n at the sample outlet of that branch channel, where n is the number of branch channels in that analysis unit. Accordingly, in an analysis unit having 2 branch channels, the pressure applied at the outlet of the branch to be blocked is P/2.

It will be appreciated that the position and fate of the molecules in the discrimination region can be monitored by additional detection regions installed, e.g., immediately upstream of the discrimination region and/or in the branch channels immediately downstream of the branch point. This information be used by the processor to continuously revise estimates of the velocity of the molecules in the channels and to confirm that molecules having selected size characteristics end up in the selected branch channel.

Solution from the branch channels is collected at the outlet ends of the analysis units. As described above, devices with a plurality of analysis units typically collect the solution from corresponding branch channels of each unit into a manifold, which routes the solution flow to an outlet port, which can be adapted for receiving, e.g., a segment of tubing or a sample tube, such as a standard 1.5 ml centrifuge tube.

The time required to isolate a desired quantity of polynucleotide depends on a number of factors, including the size of the polynucleotide, the rate at which each analysis unit can process the individual fragments, and the number of analysis units per chip, and can be easily calculated using basic formulas. For example, a chip containing 1000 analysis units, each of which can sort 1000 fragments per second, could isolate 0.1 µg of 10 kb DNA in about 2.5 hours.

VII. Operation of Other Microfabricated Devices of the Invention

Operation of a microfabricated cell sorting device is essentially as described above with respect to the polynucleotide sorting device. Since cells typically do not have predictable a net charge, the directing means are preferably ones employing a valve in the discrimination region as described above, or flow stoppage, either by valve or hydrostatic pressure.

Operation of a microfabricated analysis device is accomplished essentially as is described above, except that functions relating to sorting polynucleotide molecules into branch channels don't need to be performed. The processor of such analysis devices is typically connected to a data storage unit, such as computer memory, hard disk or the like, as well as to a data output unit, such as a display monitor, printer and/or plotter. The sizes of the polynucleotide molecules passing through the detection region are calculated and stored in the data storage unit. This information can then be further processed and/or routed to the data output unit for presentation as, e.g., histograms of the size distribution of DNA molecules in the sample. The data can, of course, be presented in real time as the sample is flowing through the device, allowing the practitioner of the invention to continue the run only as long as is necessary to obtain the desired information.

VIII. Microfabrication of Devices

Analytical devices having microscale flow channels, valves and other elements can be designed and fabricated from a solid substrate material. Silicon is a preferred substrate material because of the welldeveloped technology permitting its precise and efficient fabrication, but other materials may be used, including polymers such as polytetrafluoroethylenes. Micro machining methods well known in the art include film deposition processes, such as spin coating and chemical vapor deposition, laser fabrication or photolithographic techniques, or etching methods, which may be performed by either wet chemical or plasma processes. (See, for example, Angell et al., *Scientific American* 248:44-55 (1983) and Manz et al., *Trends in Analytical Chemistry* 10: 144-149 (1991), all incorporated herein by reference).

FIGS. 5A-5D illustrate the initial steps in microfabricating the discrimination region portion of a nucleic acid sorting device 20 (FIG. 1) by photolithographic techniques. As shown, the structure includes a silicon substrate 160. The silicon wafer which forms the substrate is typically washed in a 4:1 $H_2SO_4/H_2O_2$ bath, rinsed in water and spun dry. A layer 162 of silicon dioxide, preferably about 0.5 µm in thickness, is formed on the silicon, typically by heating the silicon wafer to 800-1200° C. in an atmosphere of steam. The oxide layer is then coated with a photoresist layer 164, preferably about 1 µm in thickness. Suitable negative-or positive-resist materials are well known. Common negative-resist materials include two-component bisarylazide/rubber resists, and positive-resist materials include polymethylmethacrylate (PMMA) and two-component diazoquinone/phenolic resin materials. See, e.g., "Introduction to Microlithography", Thompson, L. F. et al., eds., ACS Symposium Series, Washington D.C (1983).

The coated laminate is irradiated through a photomask 166 imprinted with a pattern corresponding in size and layout to the desired pattern of the microchannels. Methods for forming photomasks having desired photomask patterns are well known. For example, the mask can be prepared by printing the desired layout on an overhead transparency using a high resolution (3000 dpi) printer. Exposure is carried out on standard equipment such as a Karl Suss contact lithography machine.

In the method illustrated in FIGS. 5A-5D, the photoresist is a negative resist, meaning that exposure of the resist to a selected wavelength, e.g., UV, light produces a chemical change that renders the exposed resist material resistant to the subsequent etching step. Treatment with a suitable etchant removes the unexposed areas of the resist, leaving a pattern of bare and resist-coated silicon oxide on the wafer surface, corresponding to the layout and dimensions of the desired microstructures. In the present example, because a negative resist was used, the bare areas correspond to the printed layout on the photomask.

The wafer is now treated with a second etchant material, such as a reactive ion etch (RIE), effective to dissolve the exposed areas of silicon dioxide. The remaining resist is removed, typically with hot aqueous $H_2SO_4$. The remaining pattern of silicon dioxide (162) now serves as a mask for the silicon (160). The channels are etched in the unmasked areas of the silicon substrate by treating with a KOH etching solution. Depth of etching is controlled by time of treatment. Additional micro components may also be formed within the channels by further photolithography and etching steps, as discussed below.

Depending on the method to be used for directing the flow of molecules through the device, electrodes and/or valves are fabricated into the flow channels. A number of different techniques are available for applying thin metal coatings to a substrate in a desired pattern. These are reviewed in, for example, Krutenat, Kirk-Othmer 3rd ed., Vol. 15, pp. 241-274, incorporated herein by reference. A convenient and common technique used in fabrication of microelectronic circuitry is vacuum deposition. For example, metal electrodes or contacts may be evaporated onto a substrate using vacuum deposition and a contact mask made from, e.g., a "MYLAR" sheet. Various metals such as platinum, gold, silver or indium/tin oxide (ITO) may be used for the electrodes.

Deposition techniques allowing precise control of the area of deposition are preferred for application of electrodes to the side walls of the channels in the device. Such techniques are described, for example, in Krutenat, above, and references cited therein. They include plasma spraying, where a plasma gun accelerates molten metal particles in a carrier gas towards the substrate, and physical vapor deposition using an electron beam, where atoms are delivered on line-of-sight to the substrate from a virtual point source. In laser coating, a laser is focused onto the target point on the substrate, and a carrier gas projects powdered coating material into the beam, so that the molten particles are accelerated toward the substrate.

Another technique allowing precise targeting uses an electron beam to induce selective decomposition of a previously deposited substance, such as a metal salt, to a metal. This technique has been used to produce sub-micron circuit paths (e.g., Ballantyne et al., 1973).

Figure 6A:
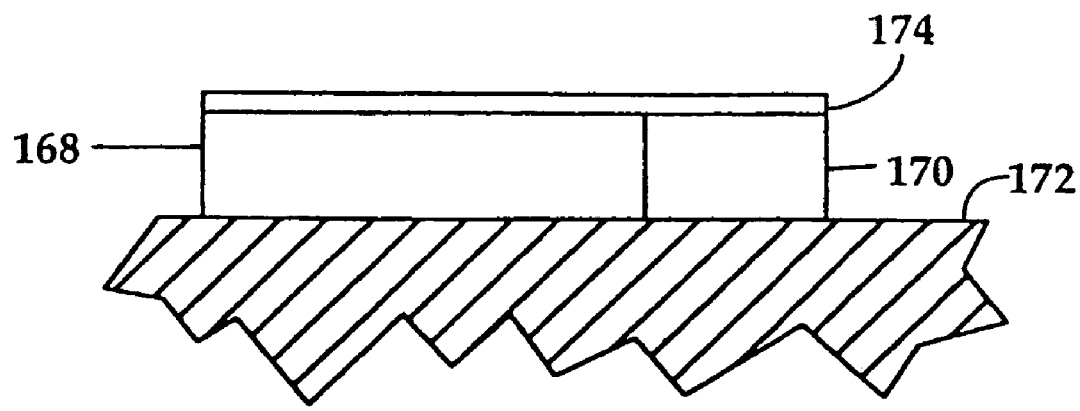
FIGS. 6A-6B show one embodiment of a valve within a branch channel of a nucleic acid sorting device, and steps in fabrication of the valve.
Figure 6B:
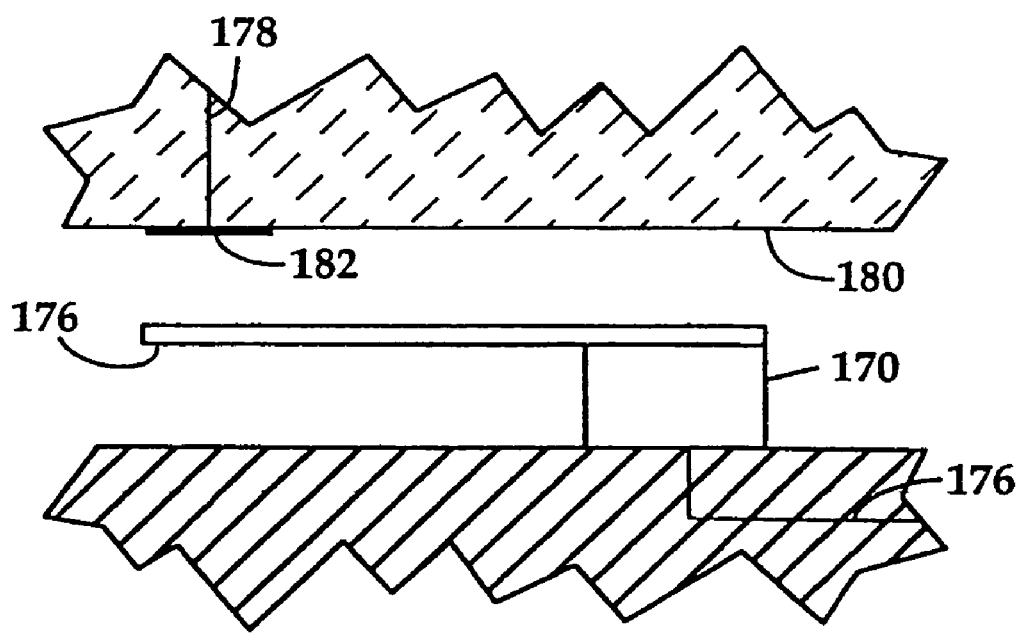

When pressure separation is to be used for discrimination of molecules, valves are used to block or unblock the pressurized flow of molecules through selected channels. A thin cantilever, for example, may be included within a branch point, as shown in FIG. 6B, such that it may be displaced towards one or the other wall of the main channel, typically by electrostatic attraction, thus closing off a selected branch channel. Electrodes are provided, as described above, on the walls of the channel adjacent to the end of the cantilever, as are suitable electrical contacts for applying a potential to the cantilever. Because the cantilever in FIG. 6B is parallel to the direction of etching, it may be formed of a thin layer of silicon by incorporating the element into the original photoresist pattern. The cantilever is preferably coated with a dielectric material such as silicon nitride, as described in Wise, et al., 1995, for example, to prevent short circuiting between the conductive surfaces.

In a separate embodiment, illustrated in FIG. 4D, a valve is situated within each branch channel, rather than at the branch point, to close off and terminate pressurized flow through selected channels. Because the valves are located downstream of the discrimination region, the channels in this region may be formed having a greater width than in the discrimination region, which simplifies the formation of valves.

Such a valve within a channel may be microfabricated, if necessary, in the form of an electrostatically operated cantilever or diaphragm. Techniques for forming such elements are well known; see, for example, Wise, et al., 1995; Aine, et al., 1986; Gravesen, et al., 1995; O'Connor, 1986; and van Lintel, 1993, incorporated herein by reference. Typical processes include the use of selectively etched sacrificial layers in a multilayer structure, or the undercutting of a layer of, e.g., silicon dioxide, via anisotropic etching. For example, to form a cantilever within a channel, as illustrated in FIGS. 6A-6B, a sacrificial layer 168 may be formed adjacent to a small section of a non-etchable material 170, using known photolithography methods, on the bottom floor of a channel, as shown in FIG. 6A. Both layers are then coated with, for example, silicon dioxide or another non-etchable layer, as shown at 172. Etching of the sacrificial layer leaves the cantilevered member 174 within the channel, as shown in FIG. 6B. Suitable materials for the sacrificial layer, non-etchable layers and etchant, respectively, include undoped silicon, p-doped silicon and silicon dioxide, and the etchant EDP (ethylene diamine/pyrocatechol).

The width of the cantilever or diaphragm should approximately equal that of the channel, allowing for movement within the channel. If desired, the element may be coated with a more malleable material, such as a metal, to allow for a better seal. Such coating may also be employed to render a non-conductive material, such as silicon dioxide, conductive.

As above, suitable electrical contacts are provided for displacing the cantilever or diaphragm towards the opposing surface of the channel. When the upper surface is a glass cover plate, as described below, electrodes and contacts may be deposited onto the glass.

It will be apparent to one of skill in the field that other types of valves or switches could be designed and fabricated, using well known photolithographic or other microfabrication techniques, for controlling flow within the channels of the device. Multiple layers of channels could also be prepared.

Operation of the valves or charging of the electrodes, in response to the level of fluorescence measured from an analyte molecule, is controlled by the processor, which receives this information from the detector. All of these components are operably connected in the apparatus, and electrical contacts are included as necessary, using standard microchip circuitry.

In preferred embodiments, an integrated semiconductor laser and/or an integrated photodiode detector are included on the silicon wafer in the vicinity of the detection region. This design provides the advantages of compactness and a shorter optical path for exciting and/or emitted radiation, thus minimizing distortion.

The silicon substrate containing the microfabricated flow channels and other components is covered and sealed, preferably with a thin glass or quartz cover, although other clear or opaque cover materials may be used. When external radiation sources or detectors are employed, the interrogation region is covered with a clear cover material to allow optical access to the analyte molecules. Anodic bonding to a "PYREX" cover slip may be accomplished by washing both components in an aqueous $H_2SO_4/H_2O_2$ bath, rinsing in water, and then heating to about 350° C. while applying a voltage of, e.g., 450V.

IV. Polynucleotide Sample Preparation

Polynucleotide samples are prepared by labeling the polynucleotide to be analyzed or sorted with a suitable optically-detectable reporter. The reporter associates with or incorporates into the DNA such that the reporter signal from a particular DNA molecule is proportional to the length of that DNA molecule.

Fluorescent dyes, particularly ones that intercalate into the polynucleotide backbone, comprise an exemplary set of optically-detectable reporters. There are a number of known dyes which selectively bind to polynucleotides. These include, but are not limited to, Hoechst 33258, Hoechst 33342, DAPI (4',6-diamidino-2-phenylindole HCl), propidium iodide, dihydroethidium, acridine orange, ethidium bromide, ethidium homodimers (e.g., EthD-1, EthD-2), acridine-ethidium heterodimer (AEthD) and the thiazole orange derivatives PO-PRO, BO-PRO, YO-PRO, TO-PRO, as well as their dimeric analogs POPO, BOBO, YOYO, and TOTO. The dimeric analogs, especially YOYO-1 and TOTO-1, are particular suitable for use with the present invention due to their high binding affinity for nucleic acids, which results in extremely high detection sensitivity. All of these compounds can be obtained from Molecular Probes (Eugene, Oreg.). Extensive information on their spectral properties, use, and the like is provided in Haugland, 1992, incorporated herein by reference.

The dyes bind at a maximum density of about one dye molecule per five base pairs. Thus, by measuring the fluorescence intensity of a molecule, its length can be determined, with a resolution of five base pairs. For a 5 Kbp molecule, this corresponds to a resolution of about 0.1%, as compared to about 10% typically obtained with gel electrophoresis.

The polynucleotide mixture is diluted in distilled water or a suitable buffer, such as TE buffer, to a concentration determined using the considerations described above. Dye is added in a 5:1 base pair/dye molecule stoichiometry.

IV. Additional Embodiments

FIG. 7 shows a device with analysis units containing a cascade of detection and discrimination regions suitable for successive rounds of polynucleotide or cell sorting. Such a configuration may be used, for example, with a polynucleotide sorting device to generate a series of samples containing "fractions" of polynucleotides, where each fraction contains a specific size range of polynucleotide fragments (e.g., the first fraction contains 100-500 bp fragments, the next 500-1000 bp fragments, and so on). In a cell sorting device, such a cascade configuration may be used to sequentially assay the cell for, e.g., 3 different fluorescent dyes corresponding to expression of three different molecular markers. Samples collected at the outlets of the different branch channels contain pools of cells expressing defined levels of each of the three markers.

While the invention has been described with reference to specific methods and embodiments, it will be appreciated that various modifications may be made without departing from the invention.

What is claimed is:

1. A method for detecting labeled molecules in a microfluidic device, said method comprising
   a) providing labeled molecules, wherein said molecules are labeled with a fluorescent dye;
   b) providing a microfluidic device comprising a channel microfabricated in a substrate, wherein said microfabricated channel comprises a detection region;
   c) transporting a solution comprising the labeled molecules through the microfluidic channel such that the molecules pass though the detection region, wherein said transporting does not comprise hydrodynamically focusing the solution with a sheath fluid;
   d) illuminating labeled molecules in the detection region with radiation from an excitation light source, wherein said radiation is of a wavelength that excites the fluorescent dye, and wherein the fluorescent dye when excited emits light of characteristic wavelengths; and
   e) detecting the emitted light,
   wherein labeled molecules outside the detection region are not illuminated with radiation from the excitation light source, and wherein, on average, only one labeled molecule occupies the detection region at a time.

2. The method of claim 1 wherein the labeled molecule is DNA.

3. The method of claim 2 wherein the microfabricated channel has a width between 1 and 10 micrometers and has a depth of between 1 and 10 micrometers.

4. The method of claim 3 wherein the detection region has a volume of between 1 femtoliter and 1 picoliter.

5. The method of claim 2 wherein the detection region has a volume of between 1 femtoliter and 1 picoliter.

6. The method of claim 1 wherein the microfabricated channel has a width between 1 and 10 micrometers and has a depth of between 1 and 10 micrometers.

7. The method of claim 1 wherein the microfabricated channel has a width between 20 and 500 micrometers and has a depth of between 20 and 500 micrometers.

8. The method of claim 1 wherein the detection region has a volume of between 1 femtoliter and 1 picoliter.

9. The method of claim 1 wherein the detection region has a volume of between 10 picoliter and 100 nanoliter.

10. A method of sizing polynucleotides in solution, comprising:
    a) flowing a continuous stream of solution containing reporter-labeled polynucleotides through a microfabricated channel comprising a detection region having a selected volume, wherein said transporting does not comprise hydrodynamically focusing the solution with a sheath fluid and where the concentration of the molecules in the solution is such that most molecules pass through the detection region one by one, and
    b) determining the size of each molecule as it passes through the detection region by measuring the level of said reporter.

11. The method of claim 10 wherein the microfabricated channel has a width between 1 and 10 micrometers and has a depth of between 1 and 10 micrometers.

12. The method of claim 11 wherein the detection region has a volume of between 1 femtoliter and 1 picoliter.

13. The method of claim 10 wherein the detection region has a volume of between 1 femtoliter and 1 picoliter.

* * * * *